(12) United States Patent
St. Louis et al.

(10) Patent No.: US 10,137,213 B2
(45) Date of Patent: Nov. 27, 2018

(54) UV DISINFECTING SYSTEM FOR A DENTAL OPERATORY

(71) Applicant: Kavo Dental Technologies, LLC, Charlotte, NC (US)

(72) Inventors: Robert Thomas St. Louis, Charlotte, NC (US); Nabil F. Dagher, Waxhaw, NC (US); Harold Thomas Lockamy, Monroe, NC (US); Douglas Gordon Knight, London (CA)

(73) Assignee: KAVO DENTAL TECHNOLOGIES, LLC, Charlotte, NC (US)

( * ) Notice: Subject to any disclaimer, the term of this patent is extended or adjusted under 35 U.S.C. 154(b) by 0 days.

(21) Appl. No.: 14/935,143

(22) Filed: Nov. 6, 2015

(65) Prior Publication Data

US 2016/0331855 A1    Nov. 17, 2016

Related U.S. Application Data

(63) Continuation-in-part of application No. 14/712,692, filed on May 14, 2015.

(51) Int. Cl.
*A61L 2/08* (2006.01)
*A61C 19/00* (2006.01)
(Continued)

(52) U.S. Cl.
CPC .............. *A61L 2/087* (2013.01); *A61B 90/70* (2016.02); *A61C 19/002* (2013.01); *A61G 15/14* (2013.01); *A61L 2/08* (2013.01); *A61L 2/10* (2013.01); *C02F 1/325* (2013.01); *E03C 1/0404* (2013.01); *A61G 15/16* (2013.01); *A61L 2202/24* (2013.01); *C02F 2201/32* (2013.01);
(Continued)

(58) Field of Classification Search
USPC ......................................................... 250/435
See application file for complete search history.

(56) References Cited

U.S. PATENT DOCUMENTS 3,872,593 A  *  3/1975  Thornton, Jr. ....... A61C 1/0007
                                                      433/101
4,009,382 A      2/1977  Gunther
(Continued)

FOREIGN PATENT DOCUMENTS

AU    2012227351       10/2012
EP    1351890 A2       10/2003
(Continued)

OTHER PUBLICATIONS

French, et al., "Optical Properties of Materials for Concentrator Photovoltaic Systems," 34th IEEE Photovoltaic Specialists Conference, Philadelphia, PA 2009 (6 pages).
(Continued)

*Primary Examiner* — Phillip A Johnston
(74) *Attorney, Agent, or Firm* — Michael Best & Friedrich LLP

(57) ABSTRACT

A disinfecting system including a delivery unit having a dental instrument holder, a dental instrument engagable with the dental instrument holder, a fluid supply line fluidly coupled to the dental instrument to provide fluid to the dental instrument, and a disinfecting device in fluid communication with at least one of the supply lines and the dental instrument.

16 Claims, 15 Drawing Sheets

(51) Int. Cl.
  *E03C 1/04*     (2006.01)
  *C02F 1/32*     (2006.01)
  *A61L 2/10*     (2006.01)
  *A61G 15/14*    (2006.01)
  *A61B 90/70*    (2016.01)
  *A61G 15/16*    (2006.01)

(52) U.S. Cl.
  CPC ...... *C02F 2303/04* (2013.01); *C02F 2307/06* (2013.01); *E03C 2201/40* (2013.01)

(56) References Cited

U.S. PATENT DOCUMENTS

| | | | |
|---|---|---|---|
| 5,304,171 A * | 4/1994 | Gregory | A61B 18/245 385/125 |
| 5,807,521 A * | 9/1998 | Franetzki | A61C 19/002 422/128 |
| 6,163,641 A | 12/2000 | Eastgate | |
| 6,740,244 B2 | 5/2004 | Baca | |
| 6,991,736 B2 * | 1/2006 | Downs | A61C 1/0061 210/668 |
| 7,160,370 B2 | 1/2007 | Baca et al. | |
| 7,169,311 B2 | 1/2007 | Sacconmanno | |
| 7,270,748 B1 | 9/2007 | Lieggi | |
| 7,683,344 B2 * | 3/2010 | Tribelsky | A61L 2/10 250/428 |
| 9,592,102 B2 * | 3/2017 | Knight | A61C 1/0076 |
| 2002/0079271 A1 | 6/2002 | Baca | |
| 2003/0076028 A1 | 4/2003 | Nieda et al. | |
| 2008/0175989 A1 | 7/2008 | Belz et al. | |
| 2009/0026385 A1 | 1/2009 | Knight et al. | |
| 2010/0264329 A1 | 10/2010 | Vardiel et al. | |
| 2010/0291502 A1 | 11/2010 | Knight | |
| 2011/0210268 A1 | 9/2011 | Dornseifer | |
| 2011/0309032 A1 | 12/2011 | Makl | |
| 2015/0008167 A1 | 1/2015 | Shturm et al. | |

FOREIGN PATENT DOCUMENTS

| | | |
|---|---|---|
| EP | 2253290 | 11/2010 |
| WO | 2010097499 | 9/2010 |
| WO | 2010104096 | 9/2010 |
| WO | 2013023666 | 2/2013 |

OTHER PUBLICATIONS

John Hopkins Medicine, <http://www.hopkinsmedicine.org/news/media/releases/latest_hands_free_electronic_water_faucets_found_to_be_hindrance_not_help_in_hospital_infection_control> dated May 20, 2015 (2 pages).

Makin, T., "Legionella Bacteria and Conditions for Its Growth and Thermal Disinfection in Stored, Pre-Heated Water for Domestic Purposes," <www.wras.co.uk/PDF_Files/Preheated_Water_Report.pdf> (5 pages).

Rice, E. et al., "The Role of Flushing Dental Water Lines for the Removal of Microbial Contaminants," Public Heath Rep. May-Jun. 2006; 121(3):270-274.

Bednarsh, H.S. et al., "Dental Unit Waterlines: Check Your Dental Water Unit IQ," Access vol. 10, No. 9, copyright 1997 by the American Dental Hygienists' Association (7 pages).

Bak, J. et al., "Disinfection of Biofilms in Tubes with Ultraviolet Light," Proceedings of World Congress of the International Ultraviolet Association (IUVA)—Sep. 2009; Amsterdam, the Netherlands, article B6-4 (9 pages).

Altkorn, R. et al., "Waveguide Capillary Cell for Low-Refractive-Index Liquids," Applied Spectroscopy vol. 51, No. 10, 1997, (pp. 1554-1558).

Yang, M. et al., "Optical properties of Teflon® AF amorphous Fluoropolymers," J. Micro/Nanolith. MEMS MOEMS 7 (3), 033010, Jul.-Sep. 2008, (10 pages).

Silva, C.F.P., "PTFE Reflectance Measurements, Modeling and Simulation for Xenon Detectors," <https://indico.cern.ch/event/102998/session/21/material/slides/0?contribId=169> The Technology and Instrumentation in Particle Physics (TIPP), Jun. 11, 2011, Chicago, IL (19 pages).

Extended European Search Report for Application No. 16168521.9 dated Mar. 1, 2017 (11 pages).

European Search Report from the European Patent Office for Application No. 16168521.9 dated Nov. 11, 2016 (7 pages).

Extended European Search Report for Application No. 16168520.1 dated Feb. 28, 2017 (10 pages).

Partial European Search Report from the European Patent Office for Application No. 16168520.1 dated Nov. 11, 2016 (6 pages).

European Patent Office Examination Report for Application No. 16168521.9 dated Jul. 10, 2018 (6 pages).

* cited by examiner

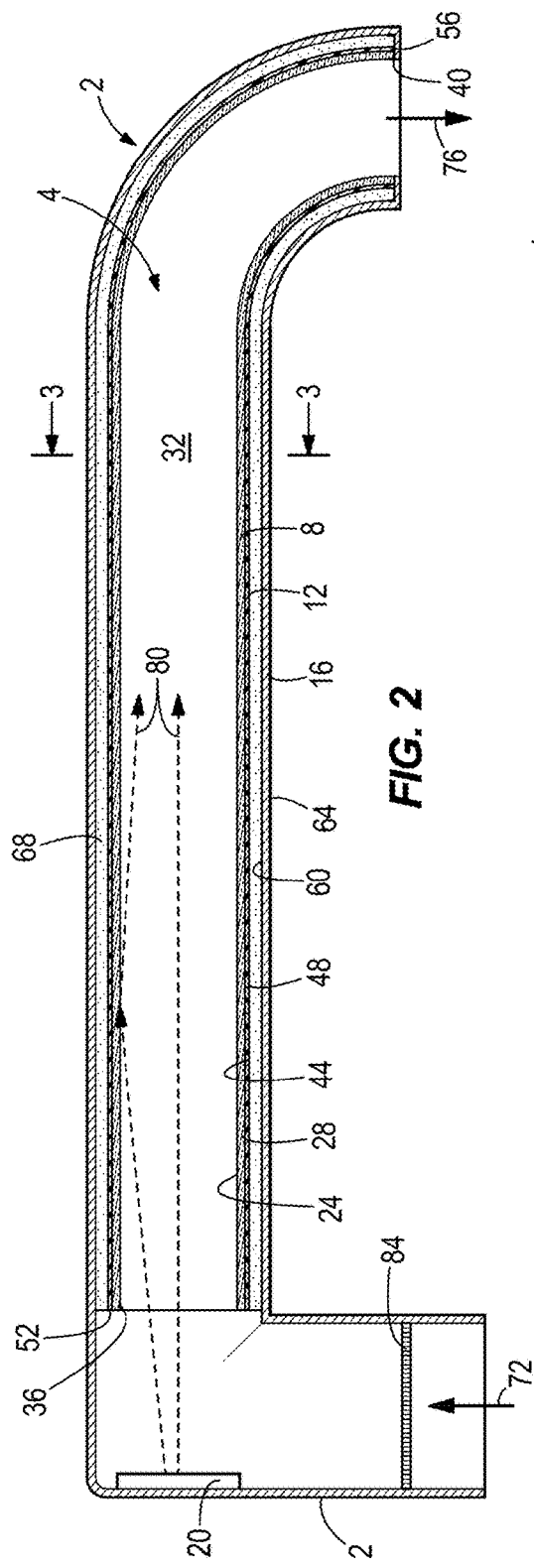
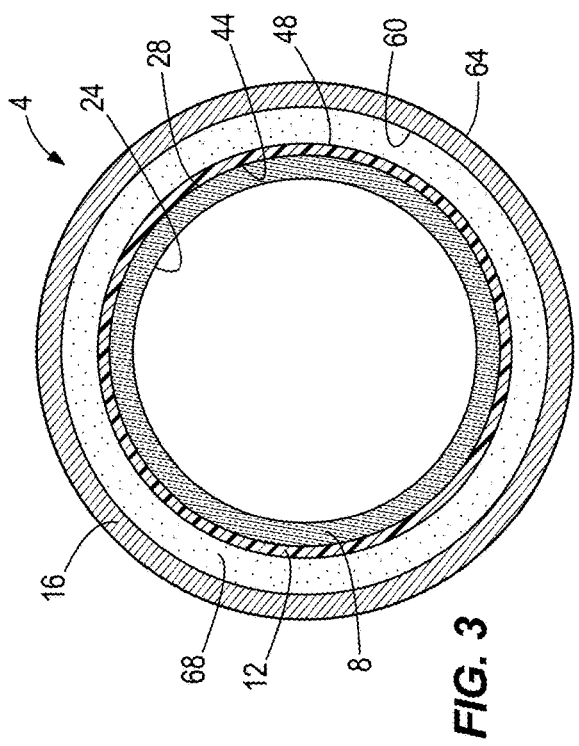

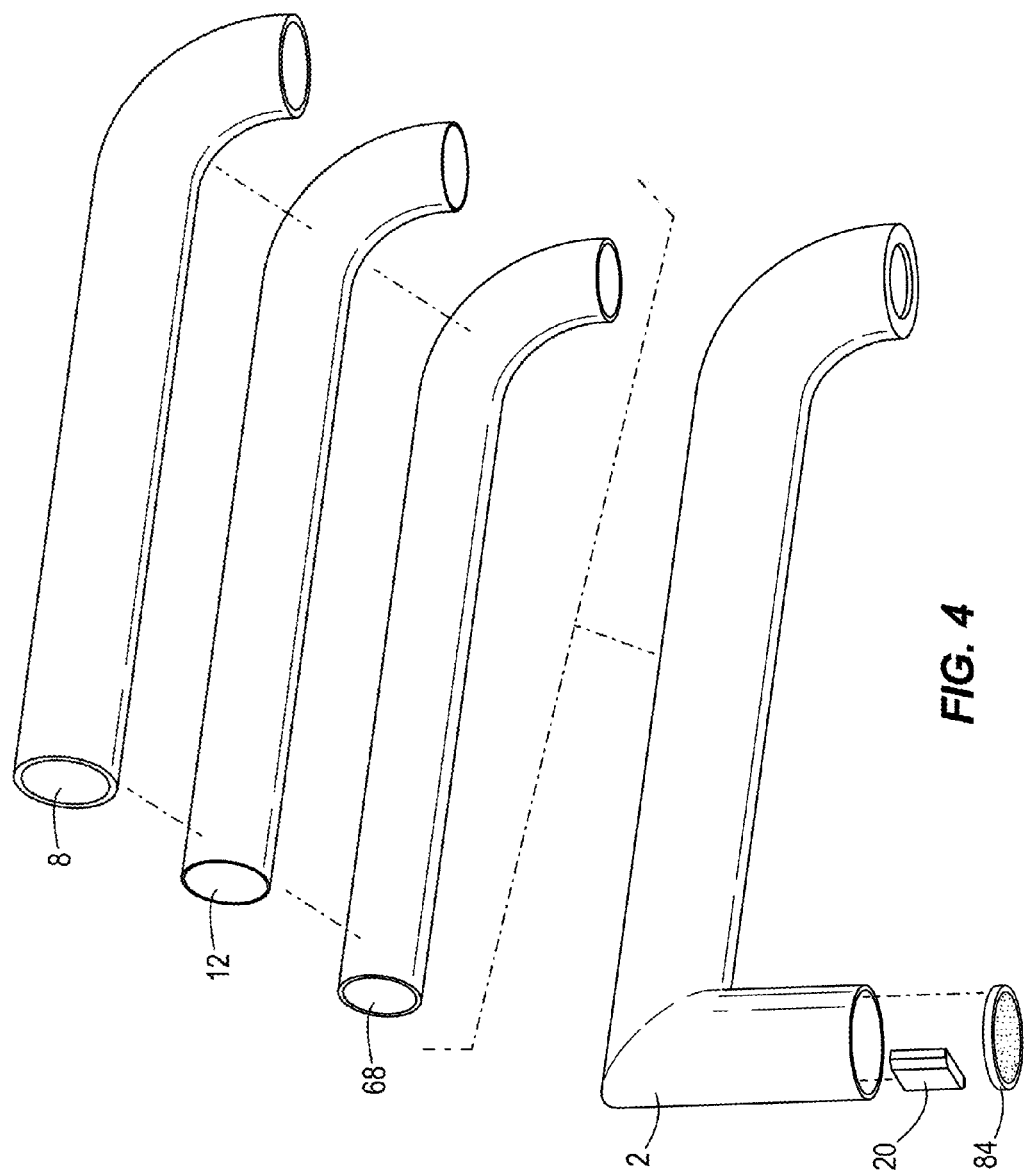

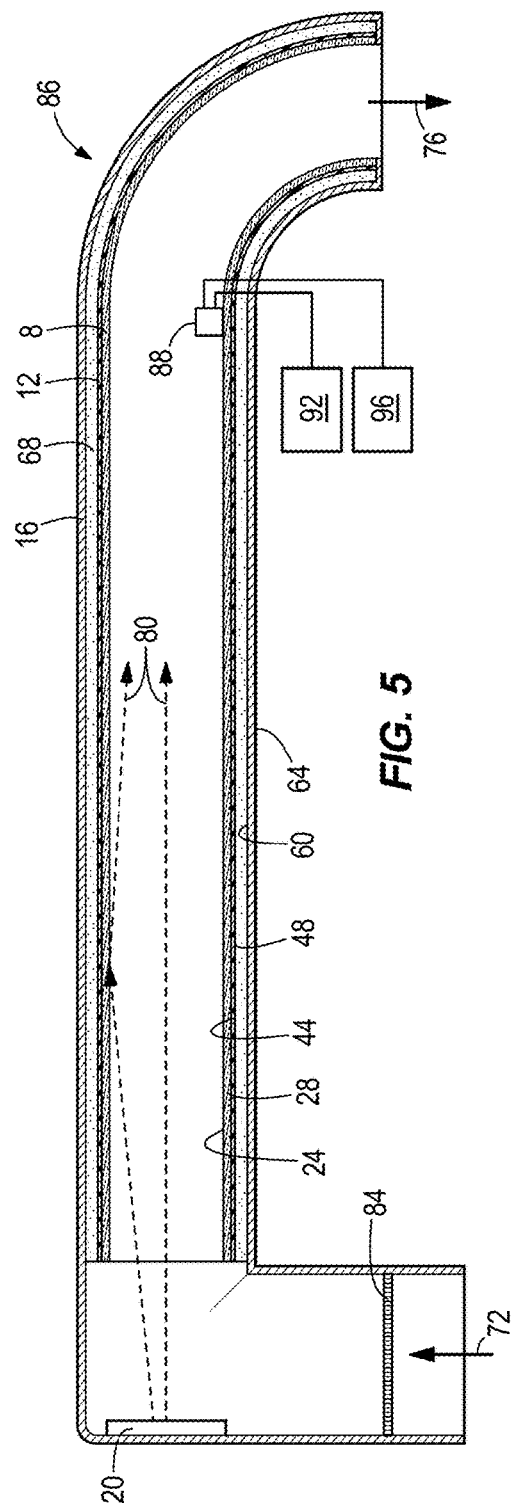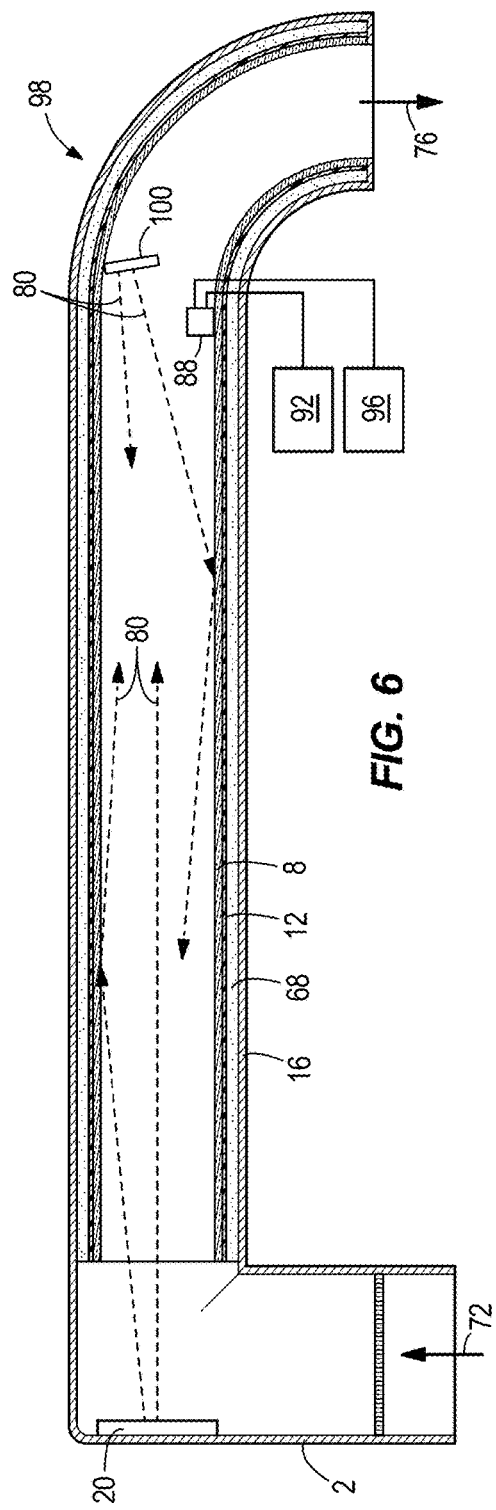

UV DISINFECTING SYSTEM FOR A DENTAL OPERATORY

CROSS-REFERENCE TO RELATED APPLICATION

This application is a continuation-in-part of U.S. patent application Ser. No. 14/712,692, filed on May 14, 2015, the entire contents of which are incorporated herein by reference.

BACKGROUND

Embodiments of the invention relate to systems and methods for disinfecting (i.e., reducing the presence of bacteria and pathogenic organisms) in a liquid.

Microbial contamination of liquids (e.g., water) within the interior surfaces of pipes and plumbing fixtures (e.g., faucets and showerheads) can be harmful to health. Contamination can be especially harmful in hospitals, dentists' offices, and similar facilities.

SUMMARY

To reduce contamination, a mechanism to inhibit the formation of biofilms on the interior surface of a liquid conduit, disinfect liquids within the conduit, or perform both operations is desirable. In one embodiment, the invention provides a disinfecting device including a conduit configured to carry a flowing liquid. The conduit has a first index of refraction. A sheath surrounds the conduit and has a second index of refraction. The second index of refraction is lower than the first index of refraction. The disinfecting device also includes a light source configured to produce disinfecting light. The light source is arranged to send the disinfecting light into the conduit.

In another embodiment, the invention provides a method of disinfecting a flowing liquid within a disinfecting device. The disinfecting device includes a conduit having a first index of refraction, a sheath surrounding the conduit that has a second index of refraction less than the first index of refraction, and a light source. The method includes directing the flowing liquid through the conduit, producing disinfecting light with the light source, and sending the disinfecting light from the light source into the conduit.

In yet another embodiment, the invention provides a faucet including a housing having an inlet and an outlet, and a quartz conduit positioned within the housing between the inlet and the outlet. The quartz conduit is configured to carry a flowing liquid and has a first index of refraction. The faucet also includes a polymer sheath positioned within the housing and surrounding the quartz conduit. The polymer sheath has a second index of refraction that is lower than the first index of refraction. The faucet further includes an ultraviolet light source configured to produce disinfecting light and arranged to send disinfecting light into the quartz conduit.

Other aspects of the invention will become apparent by consideration of the detailed description and accompanying drawings.

BRIEF DESCRIPTION OF THE DRAWINGS

FIG. 2 is a cross-sectional view of the faucet taken along section line 2-2 of FIG. 1.

FIG. 3 is a cross-sectional view of the faucet taken along section line 3-3 of FIG. 1.

FIG. 4 an exploded, perspective view of the faucet and disinfecting device of FIG. 1.

FIG. 5 is a cross-sectional view of another faucet including a disinfecting device.

FIG. 6 is a cross-sectional view of yet another faucet including a disinfecting device.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. In addition, a device or structure disclosed as being configured in a certain way can be configured in at least that way, but can also be configured in ways that are not listed. In addition, in the following description, it can be seen that various features are grouped together in various embodiments for the purpose of streamlining the disclosure. This does not mean that the claimed embodiments require more features than are expressly recited in each claim. It only means that inventive subject matter may be encompassed in fewer than all features of a single disclosed embodiment or combinations (whether full or partial) of disclosed embodiments as set forth in the written description.

Figure 1:
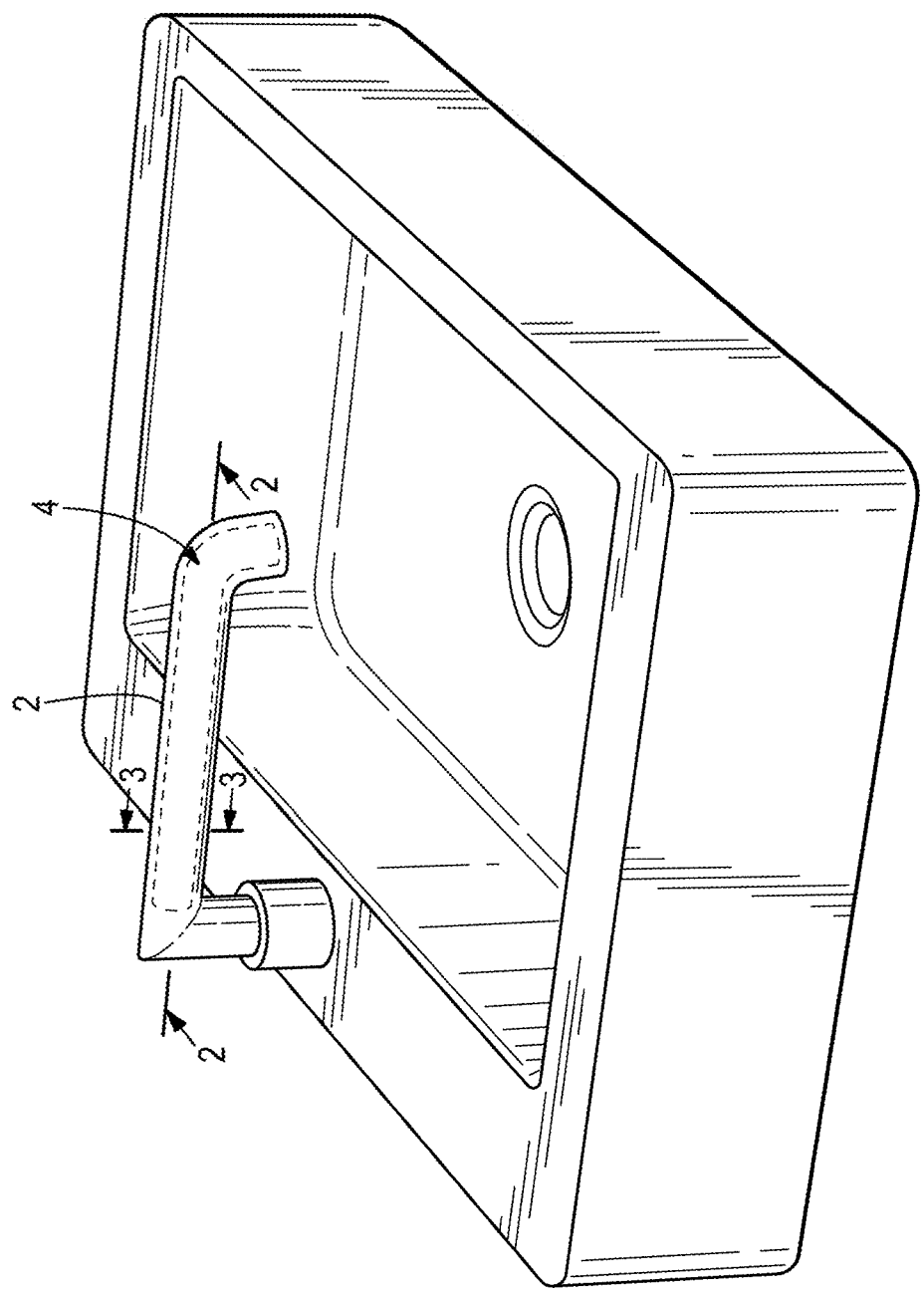
FIG. 1 is a perspective view of a sink and a faucet including a disinfecting device.

FIG. 1 illustrates a disinfecting device 4, or fluid treatment system. The disinfecting device 4 may be configured (e.g., shaped and sized) to be placed within a faucet 2, a showerhead, a dental instrument, or other device or conduit through which a liquid may flow. The illustrated disinfecting device 4 can be used in hospitals, dentist offices, public facilities, or in households in order to disinfect liquid flowing through a conduit. For example, in some embodiments, the disinfecting device 4 is used in faucets in bathroom sinks or hospital rooms. In other embodiments the disinfecting device 4 can be used in other devices, for example, within dental instruments or surgical instruments that expel water.

As shown in FIGS. 2-4, the illustrated disinfecting device 4 includes a conduit 8, a sheath 12, a housing 16, and a light source 20. The sheath 12 is coupled to the conduit 8 and at least partially surrounds the conduit 8. The housing 16 further surrounds the sheath 12 and the conduit 8. The conduit 8, the sheath 12, and the housing 16 are oriented generally parallel to one another in a longitudinal direction. The light source 20 is coupled to the housing 16 and directs light into the conduit 8.

The conduit 8 is generally cylindrical and has an inner surface 24, an outer surface 28, and a liquid channel 32. The conduit 8 further includes an inlet 36 and an outlet 40. In some embodiments, the conduit 8 can range in diameter from several centimeters to one millimeter or less. The conduit 8 can be linear or can include a curved portion. In the illustrated embodiment, the conduit 8 is composed of a UV (ultraviolet) transparent material and has a first index of refraction. For example, in a preferred embodiment, the conduit 8 is composed of quartz and has an index of refraction of about 1.505. In other embodiments, the conduit 8 may be composed of other materials and/or have a different index of refraction.

The sheath 12 substantially surrounds at least a portion of the conduit 8. The sheath 12 is generally cylindrical and includes an inner surface 44 and an outer surface 48. The illustrated sheath 12 is preferably pliable such that the inner surface 44 of the sheath 12 conforms to the outer surface 28 of the conduit 8. The sheath 12 further includes an inlet 52 and an outlet 56 that are aligned with the inlet 36 and outlet 40 of the conduit 8. The illustrated sheath 12 is generally the same length as the conduit 8, but may be longer or shorter. The sheath 12 is composed of a material with a second index of refraction that is less than the first index of refraction of the conduit 8. For example, in a preferred embodiment, the sheath 12 is composed of a polymer and, more particularly, a carbon fluoropolymer (e.g., Teflon FEP) and has an index of refraction of about 1.375. In other embodiments, the sheath 12 may be composed of other material and/or have a different index of refraction. As a consequence of the sheath 12 having an index of refraction that is less than the index of refraction of the conduit 8, the assembly of the conduit 8 and sheath 12 has certain reflective properties that will be discussed below.

The housing 16 surrounds the sheath 12 and includes an interior surface 60 and an exterior surface 64. The interior surface 60 of the housing 16 does not need to match the exact dimensions of the outer surface 48 of the sheath 12. As shown in FIG. 3, in some embodiments, a filler material 68 can occupy the space between the outer surface 48 of the sheath 12 and the housing 16 to help keep the conduit 8 in a fixed location within the housing 16. Allowing a difference in dimensions between the sheath 12 and the housing 16 is useful when fitting the conduit 8 and sheath 12 within a curved section of the housing 16, as illustrated in FIG. 2. The arrangement also simplifies the process of inserting the conduit 8 and sheath 12 into housings of different sizes and shapes, or for removal of the sheath 12 and conduit 8 from the housing 16 for cleaning. Additionally, the housing 16 includes an inlet 72 and an outlet 76. The inlet 72 and the outlet 76 of the housing 16 do not necessarily align with the inlets 36, 52 and outlets 40, 56 of the conduit 8 and sheath 12. In some embodiments, the housing 16 is formed as a liquid-carrying fixture, for example, a faucet, a showerhead, a dental instrument, or other liquid-carrying conduit.

As shown in FIG. 2, the light source 20 is coupled to the interior surface 60 of the housing 16. The light source 20 is configured to produce disinfecting light 80 (illustrated by a dotted line and arrow). The light source 20 is also configured to direct the disinfecting light 80 into the conduit 8. In a preferred embodiment, the light source 20 is coupled to the interior surface 60 of the housing 16 proximate the inlet 36 of the conduit 8 and is arranged to direct the disinfecting light 80 into the conduit 8. In other embodiments, the light source 20 can be coupled to the housing 16 proximate the outlet 40 of the conduit 8 or at a midpoint of the conduit 8. The light source 20 can alternatively be coupled to the conduit 8 or the sheath 12. In the illustrated embodiment, light source 20 is an ultraviolet light that produces ultraviolet disinfecting light 80. In some embodiments, the light source 20 includes an LED (light emitting diode). In other embodiments, the light source 20 can include multiple LEDs or an LED array. In other embodiments, other suitable types of disinfecting lights can also or alternatively be employed, such as compact electron beam UV sources.

The disinfecting light 80 produced by the light source 20 travels down the length of the conduit 8 in order to disinfect the conduit 8 and liquid flowing through the conduit 8. In the illustrated embodiment, the light 80 is able to travel down the length of the conduit 8 by being repeatedly reflected at the interface between the conduit 8 and the sheath 12. This arrangement is referred to as light guiding. By directing the disinfecting light 80 down the length of the conduit 8, the disinfecting light 80 will be in contact with the flowing liquid for a longer duration, thus increasing the effectiveness of the disinfecting light 80. Therefore, it is desirable to increase the duration of time that the disinfecting light 80 will be in contact with the conduit 8 and the flowing liquid to be disinfected. The effectiveness of the disinfecting light 80 can also vary based on the intensity of the disinfecting light 80. Therefore, it is desirable to reduce the loss of light 80 traveling through the conduit 8.

Figure 13:
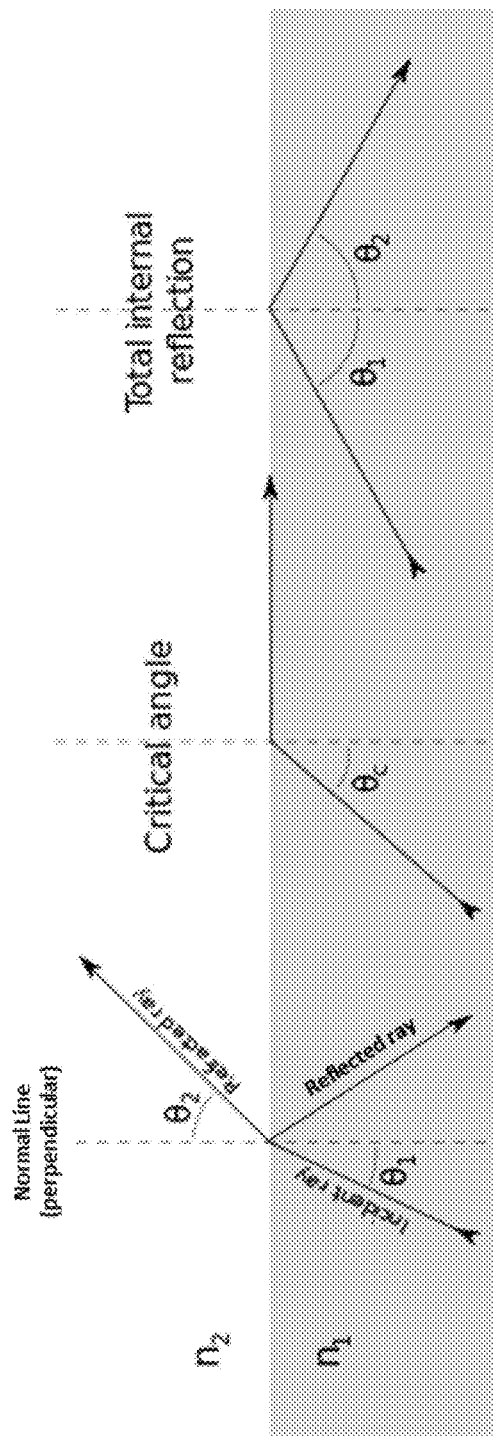
FIG. 13 is diagram showing an angle of incidence and a critical angle.

Normally, as light travels, loss of light intensity can occur when the light is either absorbed by surrounding elements or transmitted through the conduit. Loss of light by transmission or absorption can be minimized by creating an environment that allows for total internal reflection. Total internal reflection of light occurs when light passes from a material with a high index of refraction to a material with a lower index of refraction at angles of incidence greater than a critical angle. The angle of incidence $\theta_1$ is measured from the line normal (i.e., perpendicular) to the surface that the light contacts, as depicted in FIG. 13. The critical angle $\theta_C$ is the angle of incidence above which total internal reflection occurs. When total internal reflection occurs, none of the light is transmitted through the medium, but rather, all of the light is reflected. If light is traveling between two materials with a similar index of refraction, the difference may be too small to confine the light. For example, if the light is traveling in water (which has an index of refraction of 1.376) that is flowing through a Teflon tube (which has an index of refraction of 1.375), the index of refraction difference of 0.001 may be too small to confine the UV light. However, if a UV transparent material having a high index of refraction, such as quartz, is placed between the Teflon tube and the fluid, light guiding can occur while maintaining the intensity of the light.

In the illustrated embodiment, the UV transparent conduit 8 acts as the intermediate material between the polymer sheath 12 and the flowing liquid. The UV transparent conduit 8 helps to confine the light 80 and reduce the loss of light intensity by transmission. Carbon fluoropolymers have the additional advantageous property that even at angles less than the critical angle reflection is greatly enhanced as long as the index of refraction of the polymer is less than the index of refraction of the UV transparent intermediate material. More specifically, many materials will transmit refracted light upon incidence unless the angle of incidence is greater than the critical angle. Only after the angle of incidence is greater than the critical angle, will these materials will begin to reflect light. However, carbon fluoropolymers adjacent to a material with a higher index of refraction can reflect the light even at angles of incidence less than the critical angle. This reflection from the fluoropolymer can be reflected as a ray rather than the diffuse reflection more commonly seen at near normal incidence. In other words, fluoropolymers can reflect light as a ray at angles of incidence less than the critical angle, so long as the angle of incidence is approaching the critical angle. Approaching the critical angle can include any angle of incidence within 25% of the critical angle. For example, for interfaces having a critical angle of 60 degrees, light can be reflected as a ray with an angle of incidence as small as 45 degrees.

Transmission of light can also be limited or reduced by absorption. Light-absorbing compounds can accumulate in the flowing liquid and the conduit 8. The light-absorbing compounds can reduce the intensity of the light 80 as it travels over distances. Therefore, in some embodiments, the disinfecting device 4 includes a filter 84 coupled to the interior surface 60 of the housing 16 and positioned upstream from the light source 20. The filter 84 removes light-absorbing compounds that are dissolved in the liquid. For example, in some embodiments, the filter 84 is a granulated carbon filter that is inserted into the housing 16. When tap water is filtered with a carbon filter, its transparency at wavelengths greater than 225 nm, which includes the germicidal wavelength region of about 230-290 nm, is improved. When an appropriate filter is used, UV light is able to travel down the length of the conduit 8 without significant attenuation by absorption in the water. Therefore, the filter 84 allows for a greater intensity of UV light 80 to propagate through the conduit 8 for a longer distance, and as a result, increases the effectiveness of the disinfecting light 80.

FIGS. 5-9 illustrate additional embodiments of disinfecting devices. The embodiments of FIGS. 5-9 are similar to the disinfecting device 4 of FIGS. 1-4. Therefore, components or features described with respect to only one or some of the embodiments described herein are equally applicable to any other embodiments described herein.

FIG. 5 illustrates a disinfecting device 86. The disinfecting device 86 includes a sensor 88 coupled to the inner surface 24 of the conduit 8. The sensor 88 is spaced a distance from the light source 20. The sensor 88 can alternatively be coupled to the housing 16 or the sheath 12. The illustrated sensor 88 is a light sensor that is configured to sense the intensity of the light 80 propagating through the conduit 8. The sensor 88 is coupled to a power source 92 that powers the light source 20. When the sensor 88 is configured to detect a drop in the intensity of the light 80, and the drop is detected the sensor sends a signal to the power source 92 to adjust the power being supplied to the light source 20. Adjusting the power supplied to the light source 20 will help adjust the output of disinfecting light 80 from the light source 20.

The sensor 88 can further be connected to a warning system 96 that is configured to warn or notify a user to replace the filter 84. When the filter 84 is saturated, the filter 84 may no longer effectively remove UV-absorbing compounds from the liquid. As a result, the transmittance of light 80 through the liquid will drop. This drop in transmittance will be detected as a decrease in light intensity by the sensor 88. The sensor 88 is configured to send a signal to the warning system 96 in order to activate a warning signal to notify a user to replace the filter 84. The warning system 96 can include, for example, a light or a sound emitting device that produces visual (e.g., flashes) or audible (e.g., beeps) indications, respectively. In some embodiments, the sensor 88 can be used for both sending a signal indicating that the filter 84 should be replaced, and for sending a signal indicating that the amount of power being supplied to the light source 20 should be adjusted.

FIG. 6 illustrates a disinfecting device 98. The disinfecting device 98 includes a mirror 100 that can also be incorporated into the disinfecting device 98 to either direct the disinfecting light 80 into the conduit 8, or to reflect the disinfecting light 80 back into the conduit 8. For example, the light source 20 can be coupled at a first end of the conduit 8, and the mirror 100 can be coupled at a second end of the conduit 8. Light 80 generated by the light source 20 will travel through the conduit 8 and eventually reach the mirror 100 where the mirror 100 will reflect the light 80 back into the conduit 8. Mirrors can be placed on the opposite end of the conduit 8 from the light source 20, or they can be placed around a curved portion of the conduit 8. Reflecting the disinfecting light 80 back into the conduit 8 will increase the overall light 80 intensity within the conduit 8, which will increase the disinfecting effectiveness of the light 80. Reflecting the light 80 will also allow the disinfecting light 80 to reach parts of the conduit 8 that may not have been reached while the light 80 traveled through the conduit 8 in the first direction. For example, if the conduit 8 is curved or otherwise defines a tortuous path, the mirror 100 can help direct the disinfecting light 80 through curves and bends in the conduit 8. In some embodiments, the disinfecting device 98 can include more than one mirror.

Figure 7:
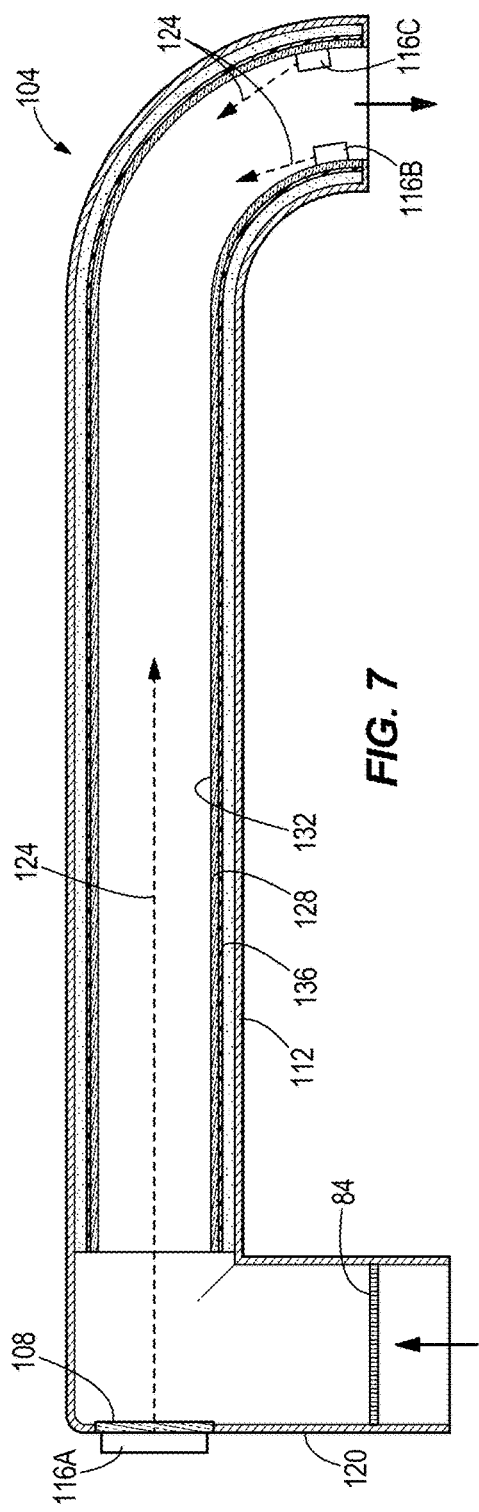
FIG. 7 is a cross-sectional view of still another faucet including a disinfecting device.

FIG. 7 illustrates a disinfecting device 104 including a UV transparent window 108 coupled to a housing 112. The window 108 allows for a light source 116 to be coupled to an exterior surface 120 of the housing 112 while still directing disinfecting light 124 into a conduit 128. In the illustrated embodiment, the disinfecting device 104 includes multiple light sources 116A-C. One light source 116A is coupled to the exterior surface 120 of the housing 112, and additional light sources 116B-C are coupled to an inner surface 132 of the conduit 128. In particular, the first light source 116A is positioned proximate an inlet of the conduit 128, while the second and third light sources 116B-C are positioned proximate an outlet of the conduit 128. The conduit 128 and the sheath 136 include a curved section that extends through a curved section of the housing 112. The light sources 116B-C help direct disinfecting light 124 through the curved section of the housing 112. The additional disinfecting light 124 will increase the overall light intensity and improve the effectiveness of the disinfecting device 104.

Figure 8:
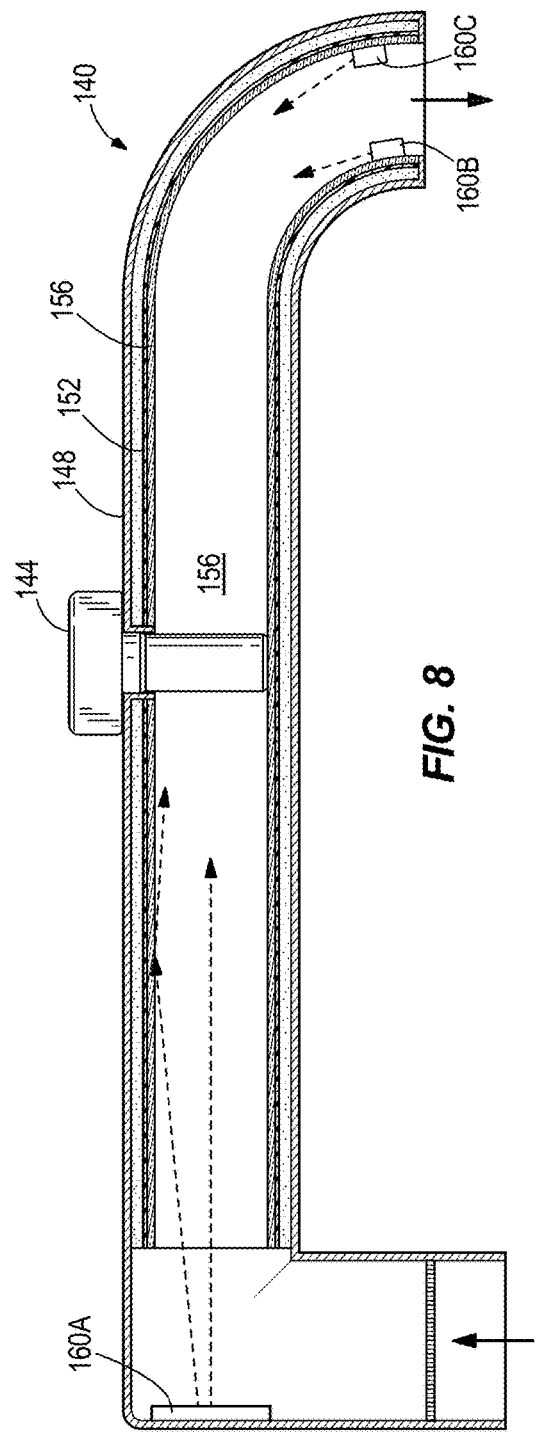
FIG. 8 is a cross-sectional view of a faucet including a valve and a disinfecting device.

FIG. 8 illustrates a disinfecting device 140. The disinfecting device 140 includes a valve 144 that controls flow of liquid through a conduit 156. In the illustrated embodiment, the valve 144 protrudes into a housing 148 and through a sheath 152 and the conduit 156. Because pathogenic organisms can grow on the surface of the valve 144, light sources 160A-C are placed on both sides of the valve 144 to irradiate the surface of the valve 144 from various angles. This arrangement ensures that all portions of the conduit 156 are exposed to the disinfecting light 164, despite the presence of the valve 144 or other elements that may block light 164.

Figure 9:
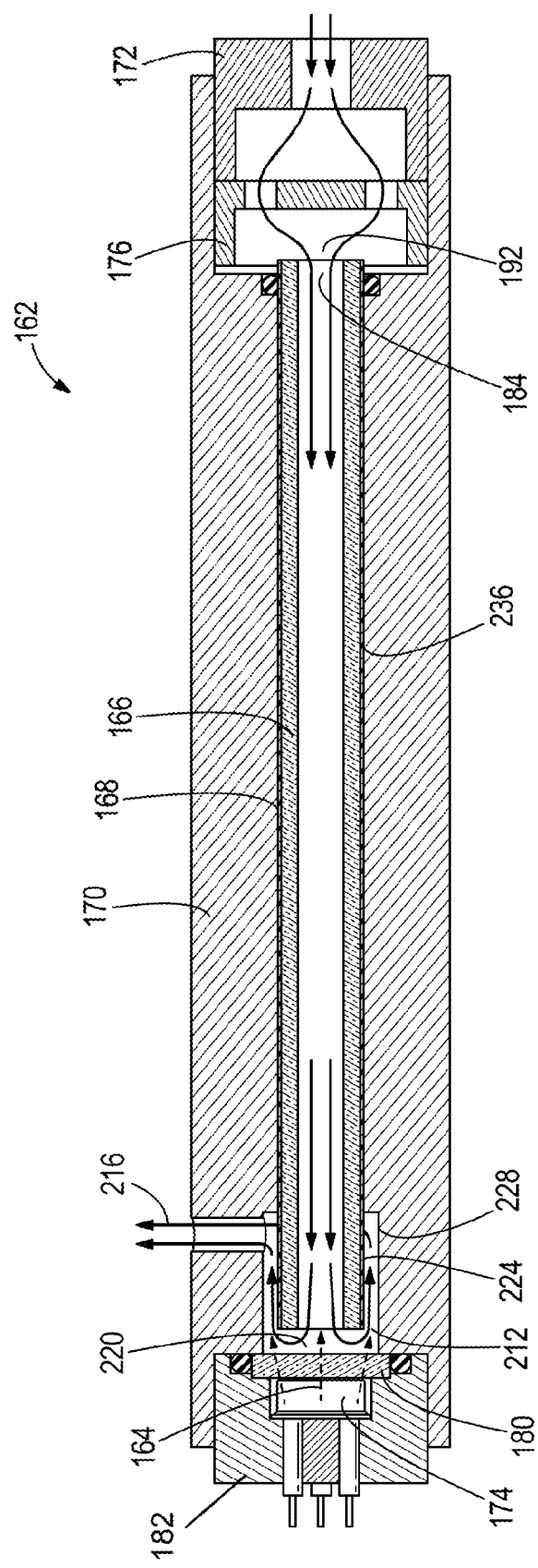
FIG. 9 is a cross-sectional view of another disinfecting device including a liquid inlet distributor and a liquid collection chamber.
Figure 10:
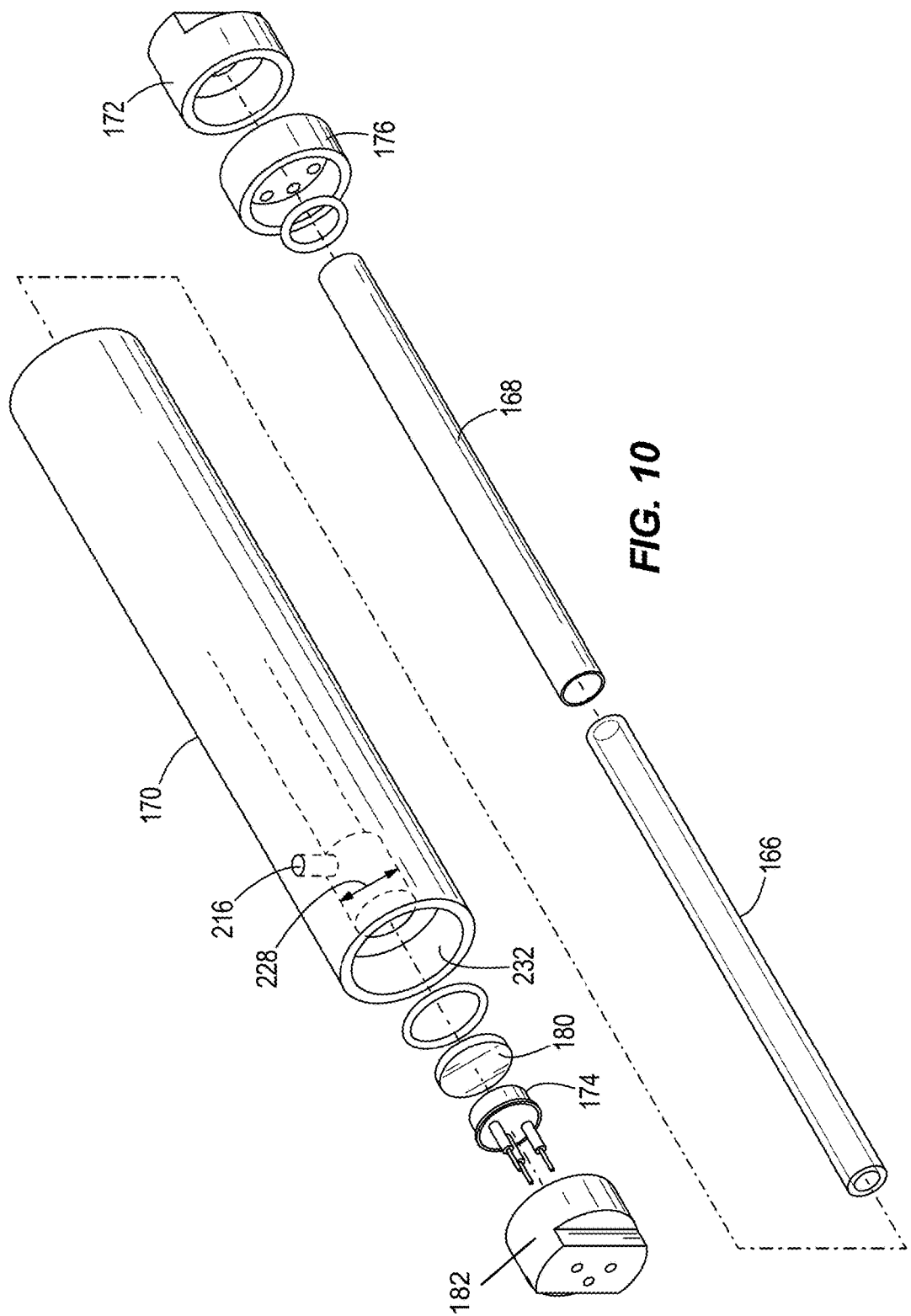
FIG. 10 is an exploded, perspective view of the disinfecting device of FIG. 9.
Figure 11A:
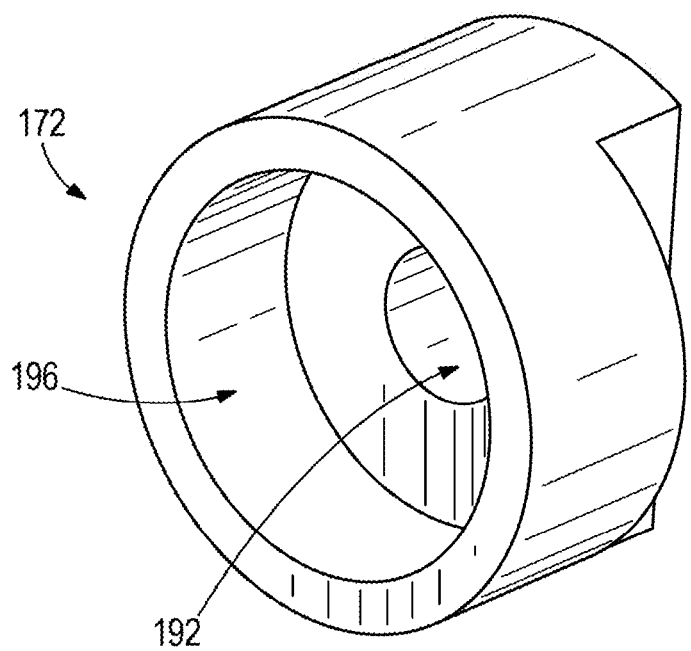
FIG. 11A is a perspective view of a liquid inlet cap for use with the disinfecting device of FIG. 9.
Figure 11B:
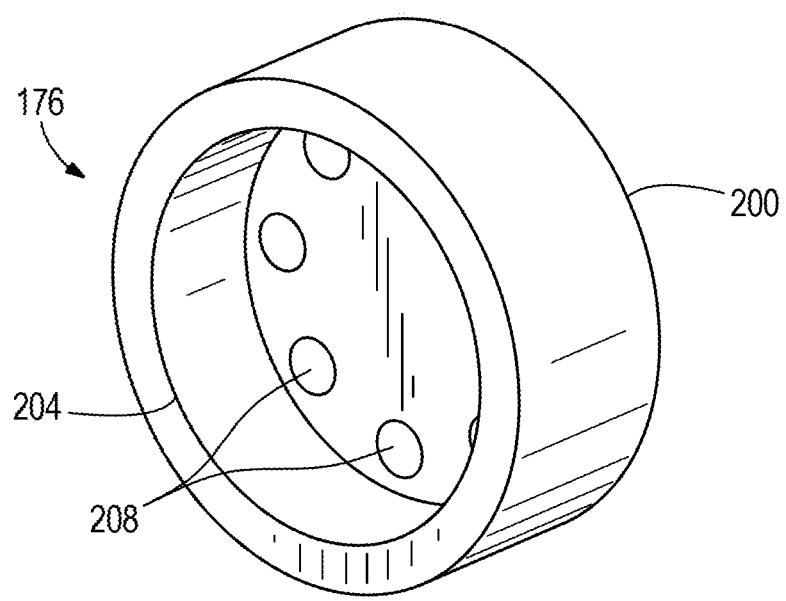
FIG. 11B is a perspective view of a liquid inlet flow distributor for use with the disinfecting device of FIG. 9.

FIGS. 9-11 illustrate another embodiment of the invention in the form of a disinfecting device 162. The disinfecting device 162 is suitable, for example, for use with low-flow applications, for example, point-of-use disinfection of dental supply lines or for tabletop water disinfection systems. Similar to the disinfecting device shown in FIG. 2, the illustrated disinfecting device 162 includes a conduit 166, a sheath 168, a housing 170, and a light source 174. The illustrated device 162 also includes a window 180, an end cap 182, a liquid inlet cap 172, and a liquid inlet flow distributor 176. The end cap 182 houses the window 180 and the light source 174. The end cap 182 is positioned downstream of the conduit 166 and the sheath 168. The inlet cap 172 and the distributor 176 are coupled to the housing 170 upstream of the inlet 184 of the conduit 166. With reference to FIG. 11A, the liquid inlet cap 172 includes a liquid inlet portion 192 and a liquid inlet flow chamber 196. The liquid inlet flow chamber 196 has a diameter that is greater than a diameter of the liquid inlet portion 192. As shown in FIGS. 9 and 10, the flow distributor 176 is positioned proximate to the inlet flow chamber 196 of the liquid inlet cap 172. With reference to FIG. 11B, the flow distributor 176 is cylindrical and includes a closed end 200 and an open end 204. The closed end 200 includes circular openings 208 near the outer circumferential edge of the distributor 176.

Referring to FIG. 9, the liquid flow distributor 176 forces the liquid to flow radially outwards from the inlet flow chamber 196. Specifically, the liquid is forced through the openings 208 in the flow distributor 176 located near the outermost edges of the flow distributor 176. The liquid then flows inward into the inlet 184 of the conduit 166, as shown by dashed lines. Providing the flow distributor 176 at the inlet 184 of the conduit results in a slower, more even velocity of liquid flow, resulting in a more uniform UV dose distribution. Although FIG. 11B illustrates one specific type of flow distributor, it should be apparent than other types of flow distributors may also or alternatively be used.

With continued reference to FIGS. 9-11, the illustrated embodiment of the disinfecting device 162 further includes a liquid collection chamber 212 located downstream from the outlet 216 of the conduit 166. The liquid collection chamber 212 defines a cavity 220 at least partially surrounding the outlet 216 of the conduit 166. The collection chamber 212 includes an inner diameter 224 and an outer diameter 228. The collection chamber 212 can be formed by creating a recess 232 in the housing 170 near the conduit 166. The inner surface of the housing 170 that defines the recess 232 also defines the outer diameter 228 of the collection chamber 212. An outer surface 236 of the sheath 168 that extends into the recess 232 defines the inner diameter of the collection chamber 212.

To help increase the amount of disinfecting light 164 propagating down the length of the conduit 166, it is desirable to reduce the distance between the light source 174 and the conduit 166, without obstructing the free flow of liquid out of the conduit 166. The collection chamber 212 allows for a reduced distance between the light source 174 and the conduit 166 by allowing liquid to flow radially outward from the conduit 166 and gather in the collection chamber 212 without blocking the continual flow of liquid through the conduit 166. The collection chamber 212 therefore creates a uniform radial flow of the fluid exiting the conduit 166. The uniform radial flow out of the conduit 166 allows for plug flow of the liquid all the way to the inlet 184 end of the conduit 166 so that UV dose distribution is generally uniform.

Figure 12:
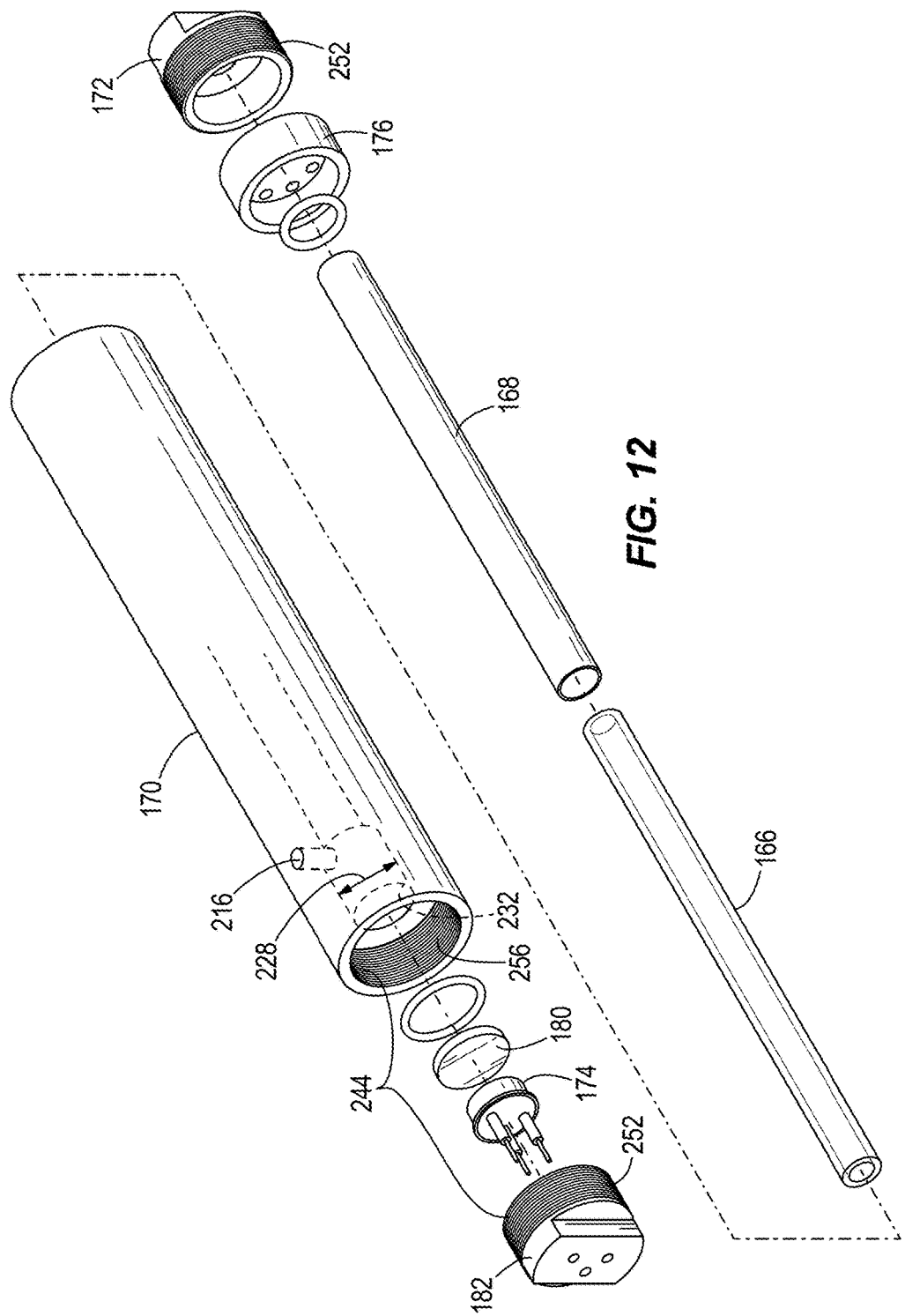
FIG. 12 is an exploded, perspective view of a disinfecting device having a removable cap.

Some embodiments of the invention include features that permit cleaning and replacement of the conduit 166 and sheath 168. FIG. 12 illustrates an embodiment in which the caps 172 and 182 and light source 174 are detachable or removable from the housing 170 to provide access to the conduit 166 and sheath 168. In one configuration, the cap 182 and housing 170 include threads 252 and 256, respectively, to permit the cap 182 to be screwed into and out of the housing 170. When the cap 182 is unscrewed from the housing 170, a user may access the conduit 166 and sheath 168 for cleaning, for example, by inserting a brush or pipe cleaner (not shown) into the conduit 166. The cap 172 may be similarly screwed into or out of the housing 170 (although complimentary threads in the housing 170 to receive the threads 252 of the cap 172 are not shown). Instead of using a threaded connection, a quick connect fitting could be used to provide a connection between the caps 172 and 182 and the housing 170. Other types of connections may also be used, for example, a snap-fit connection, a detent connection, or a connection with a cam can be utilized. Instead of cleaning the conduit 166 after removing one or both of the caps 172 and 182, the conduit 166 and sheath 168 can be removed entirely from the housing 170 and replaced.

Figure 14:
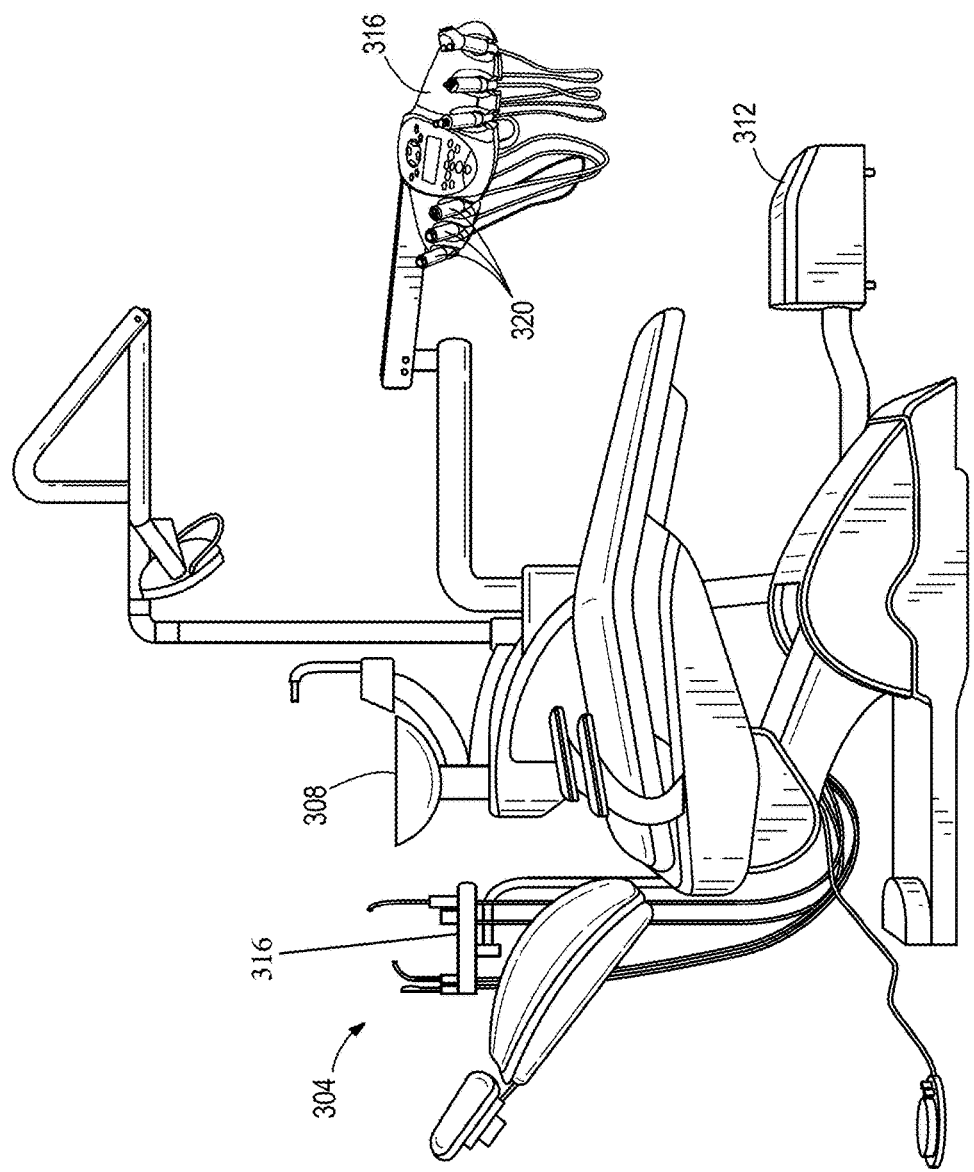
FIG. 14 is a perspective view of a dental chair situated in an exemplary dental operatory that includes, among other things, a handpiece system, lighting, and plumbing.
Figure 16:
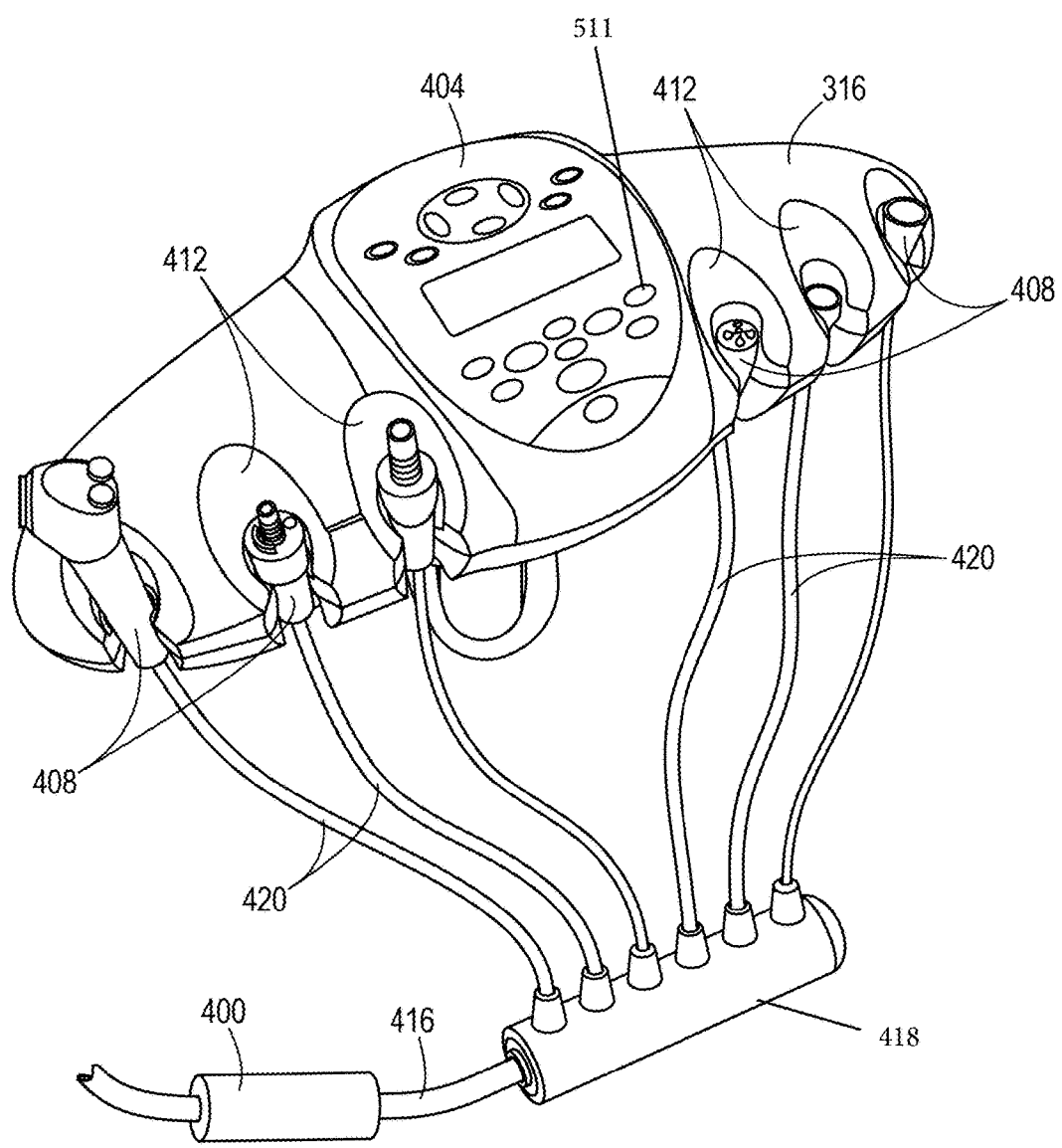
FIG. 16 is a perspective view of a delivery unit including a disinfecting device.
Figure 17:
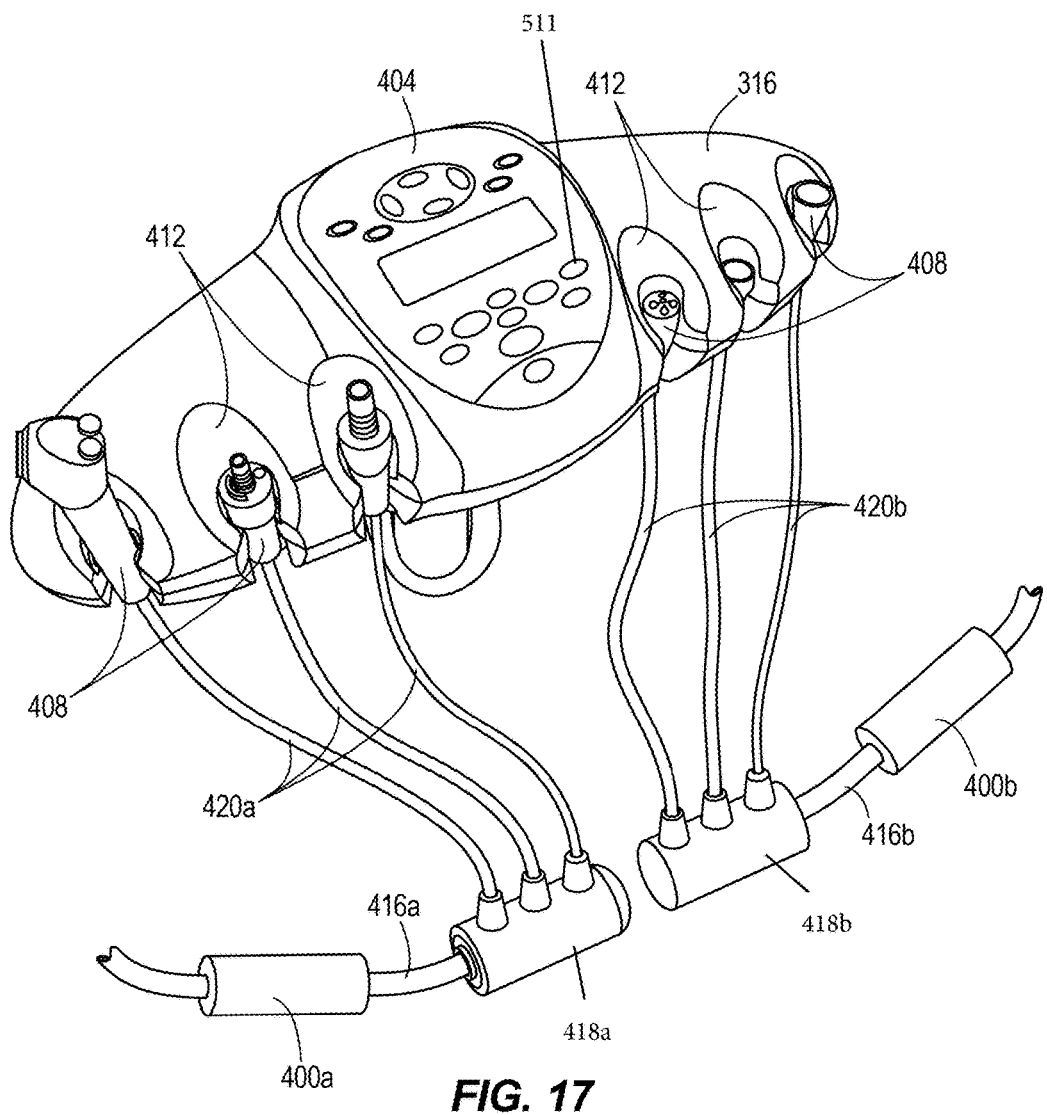
FIG. 17 is a perspective view of another delivery unit including a disinfecting device.
Figure 18:
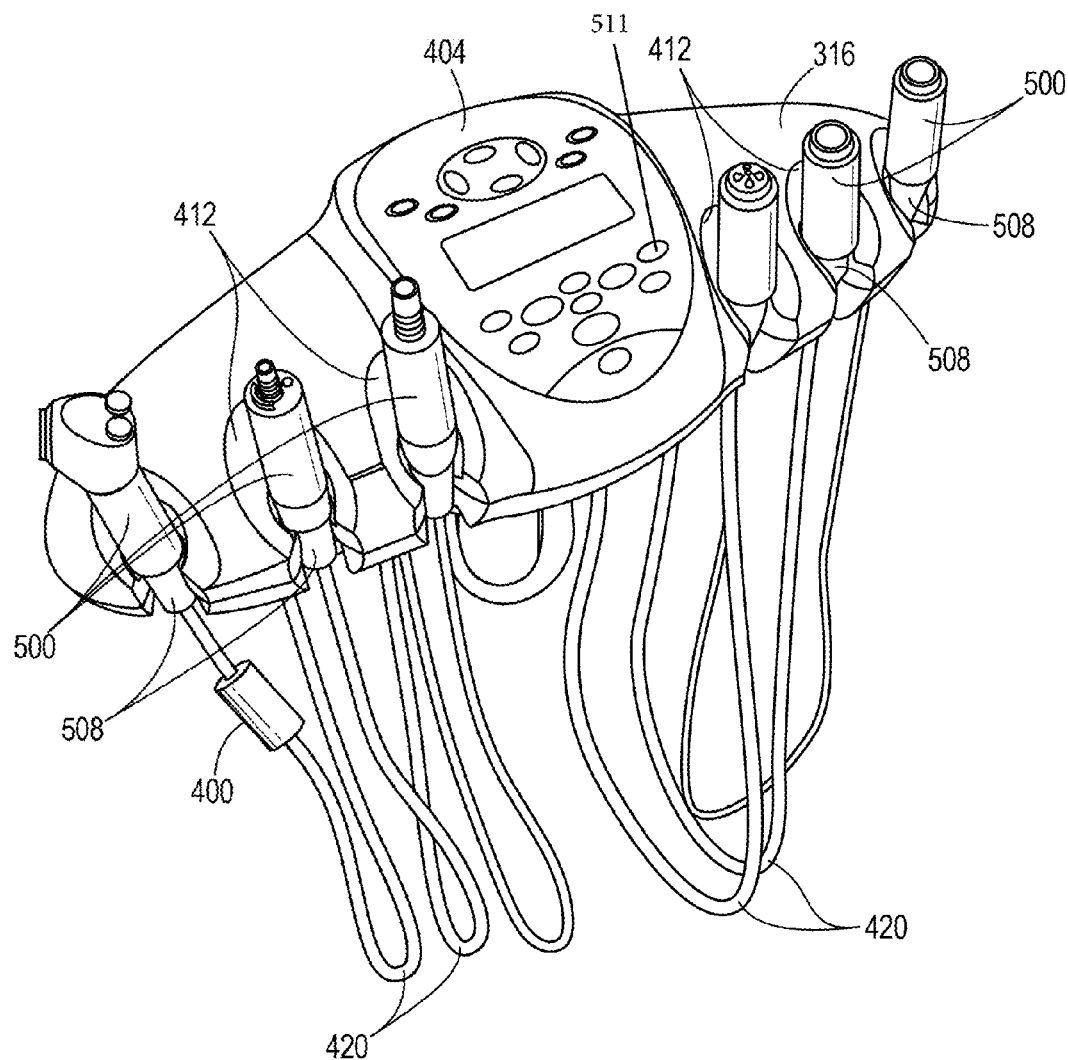
FIG. 18 is a perspective view of another delivery unit including a disinfecting device.

FIGS. 14-18 illustrate embodiments of disinfecting systems that include variously configured disinfecting devices, namely disinfecting device 300 (FIG. 15), disinfecting device 400 (FIGS. 16 and 18), disinfecting devices 400*a*, 400*b* (FIG. 17), and disinfecting devices 508 (FIG. 18). FIG. 14 illustrates a dental chair 304 in a dental operatory that includes various equipment and fixtures. In the embodiment illustrated, the dental operatory includes a sink or spittoon 308, a junction box 312, and at least one delivery unit 316 for supporting a plurality of dental instruments 320 (e.g., handpieces) and/or couplings for attaching dental instruments. As illustrated in FIG. 14, in some embodiments two delivery units 316 are provided, one of the delivery units being a rear mounted treatment unit on the dental chair 314 (e.g., for use by a dental assistant to transfer of water to a patient). As will be explained in greater detail below, the disinfecting devices 300, 400, 400*a*, 400*b*, and 508 are adapted to disinfect fluid flowing through and/or to the equipment and fixtures of the dental operatory. The disinfecting devices 300, 400, 400*a*, 400*b*, and 508 can be removably coupled to the various equipment and fixtures by quick-connect couplings or by other types of connectors or couplings. The quick-connect couplings facilitate relatively fast connection and disconnection of the disinfecting device 300, 400, 400*a*, 400*b*, and 508 for cleaning, replacement, and other purposes. The equipment and fixtures in the dental operatory can be retrofitted with the disinfecting device 300, 400, 400*a*, 400*b*, and 508.

Figure 15:
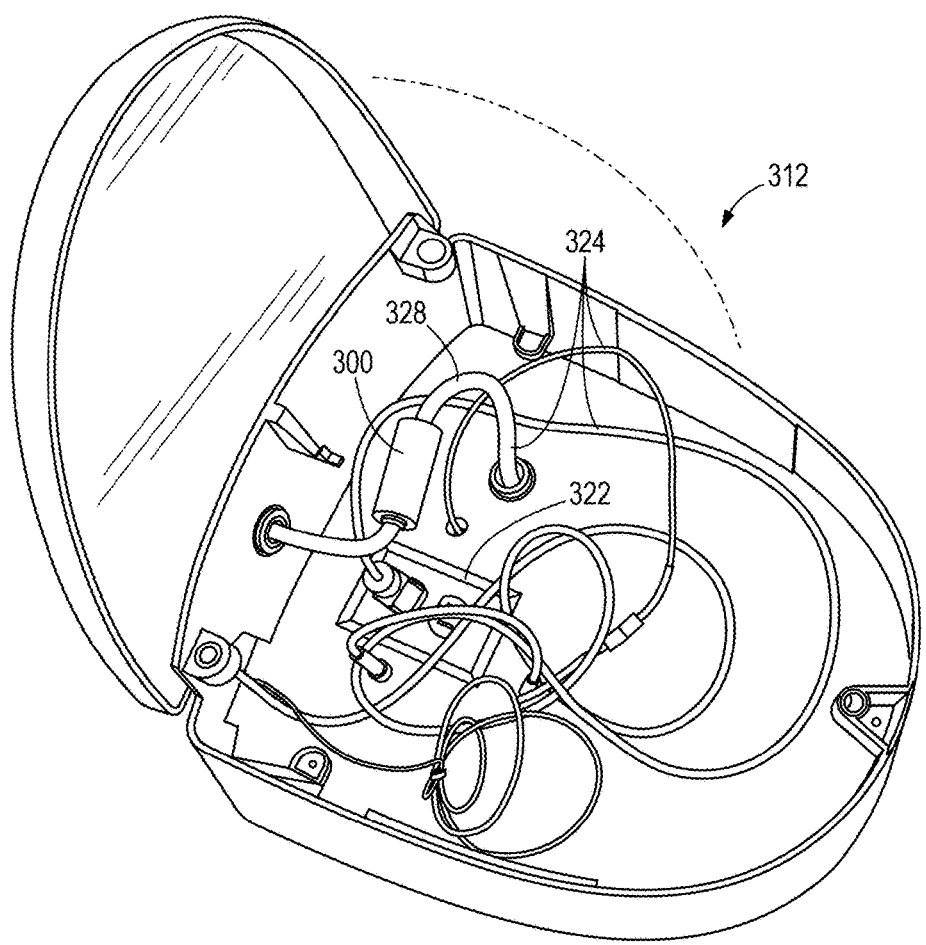
FIG. 15 is a perspective view of a junction box including a disinfecting device.

FIG. 15 illustrates the interior of an exemplary junction box 312. The junction box 312 includes a power source 322 and various supply lines 324 that provide, for example, electricity, water, and air to the dental instruments 320. In one embodiment, the disinfecting device 300 is positioned in a fluid supply line 328 in a series manner. In some embodiments, a source of electric power for a disinfecting UV light is provided within the fluid supply line 328. The disinfecting device is positioned internally to or within the junction box 312. The fluid supply line 328 provides fluid to the dental instruments 320. The dental instruments 320 are fluidly coupled to the fluid supply line 328 and located externally to the junction box 312.

FIGS. 16-18 illustrate the delivery unit 316 in greater detail. The delivery unit 316 includes a control panel 404, and holds a plurality of couplings 408 (e.g., quick-connect) for dental instruments (some of the heads of the dental instruments are not shown) via a plurality of dental instrument holders 412. In other words, the couplings 408 are engaged or held by the instrument holders 412. FIG. 16 shows the disinfecting device 400 positioned along a main fluid line 416, the main fluid line 416 being coupled via a manifold 418 to a plurality of individual fluid lines 420 that provide fluid to each respective coupling 408. In some embodiments a source of electrical power for a disinfecting UV light is provided within in one or more of the fluid lines 420. In the embodiment of FIG. 16, the manifold 418 receives fluid from the main fluid line 416 and distributes or provides fluid to the individual fluid lines 420 that each lead to a single coupling 408.

In some embodiments, two or more disinfecting devices 400 can each be used to distribute or provide fluid to the couplings 408. For example, in FIG. 17 two disinfecting devices 400a and 400b are each positioned between along a main fluid line 416a and 416b, the main fluid lines 416a and 416b being coupled via a manifold 418a and 418b to a plurality of individual fluid lines 420a and 420b. In this embodiment each disinfecting device 400a and 400b distributes fluid to three couplings 408. Greater or fewer disinfecting devices 400 may be used with greater or fewer couplings 408 and/or instruments.

FIG. 18 is another illustration of the delivery unit 316. However, in the embodiment of FIG. 18, each coupling 500 for a dental instrument is individually fitted with a disinfecting device 508. As noted above, the delivery unit 316 includes a control panel 404, and holds a plurality of couplings 500 via a plurality of dental instrument holders 412. FIG. 18 shows multiple disinfecting devices 508, one for each coupling 500. In this embodiment, each coupling 500 receives fluid from an individual fluid line 420 and a disinfecting device 508 is positioned along the individual fluid line 420 adjacent each coupling 500. With continued reference to FIG. 18, in some embodiments one or more of the disinfecting devices 400 are positioned along the dental instrument's individual fluid line 420 (e.g., as opposed to along a main line as illustrated in FIG. 16), the disinfecting device or devices 400 being spaced from the coupling 500. The disinfecting device 400 and/or 508 may be powered by the fluid line 420 (e.g., in some embodiments a source of electric power for a disinfecting UV light in the disinfecting device 400 and/or 508 is provided within the fluid line 420). In some embodiments the disinfecting device 400 replaces the disinfecting device 508. In some embodiments, as illustrated in FIG. 18, both the disinfecting device 400 and the disinfecting device 508 are used for at least one of the couplings 500.

With reference to FIGS. 16-18, in some embodiments the delivery unit 316 includes an activation element 511 that is used to both turn on and off a water supply, as well as to turn on and off the disinfecting system (e.g., to turn off one or more of the disinfecting devices 300, 400, 400a, 400b, and 508). Thus, when water is not needed, energy is saved by turning off the disinfecting system. In the illustrated embodiment the activation element 511 is a button. However, in some embodiments the activation element 511 is a trigger that is activated (e.g., turned on) when a dental instrument and/or its coupling (e.g., coupling 408) is removed from its holder (e.g., holder 412). In some embodiments the activation element 511 is mechanical or electrical (e.g., is an air actuated activation element, or an optical/proximity sensor). Other embodiments include different types of activation elements 511.

In some embodiments, the disinfecting UV light for one or more of the disinfecting devices 300, 400, 400a, 400b, and 508 is from an LED source, making the disinfecting device an LED disinfecting device. In some embodiments, the disinfecting UV light is from an electron beam source, making the disinfecting device an electron beam disinfecting device. In some embodiments, the disinfecting UV light is from a miniature xenon flash lamp source, making the disinfecting device a miniature xenon flash lamp disinfecting device. Other embodiments utilize different disinfecting UV light sources.

Various features and advantages of the invention are set forth in the following claims.

What is claimed is:
1. A fluid treatment system comprising:
a dental instrument adapted to receive a fluid;
a fluid supply line configured to be coupled to the dental instrument and to provide fluid to the dental instrument for use of the fluid during a dental procedure, and
a UV source positioned to be in fluid communication with the fluid such that UV light from the UV source disinfects the fluid;
wherein the UV source includes
a conduit adapted to carry the fluid and having a first index of refraction, the conduit having an outside surface;
a pliable sheath surrounding the conduit, the sheath having an inside surface in contact with the outside surface of the conduit, the sheath having a second index of refraction, the second index of refraction being lower than the first index of refraction, and
a light source configured to produce UV light and arranged to send the UV light into the conduit.
2. The fluid treatment system of claim 1, wherein the UV source is selected from a group consisting of an LED source, an electron beam source, and a miniature xenon flash lamp source.
3. A fluid treatment system comprising:
a delivery unit including a dental instrument holder;
dental instruments engagable with the dental instrument holder;
a fluid supply line in fluid communication with the dental instruments to supply fluid to the dental instruments for use of the fluid during a dental procedure, the fluid supply line including a main fluid supply line and a plurality of individual fluid supply lines extending from the main fluid supply line to the dental instruments;
a UV source coupled along the fluid supply line, the UV source positioned to be in fluid communication with the fluid such that UV light from the UV source disinfects the fluid; and
a junction box, wherein the main fluid supply line is disposed at least partially within the junction box, wherein the UV source is coupled to the main fluid supply line within the junction box, and wherein the main fluid supply line is coupled to the plurality of individual fluid supply lines with a manifold.
4. The fluid treatment system of claim 3, wherein the UV source includes a cylindrical housing, a cylindrical sheath disposed within the housing, and a cylindrical conduit disposed within the sheath, wherein the sheath is pliable, and has an inner surface in contact with an outer surface of the conduit, and wherein at one end of the sheath, a radial gap is disposed between the sheath and the housing, the gap defining a collection chamber for the fluid.

5. The fluid treatment system of claim 3, wherein the UV source is one of a plurality of UV sources, each of the plurality of UV sources positioned upstream of one of the dental instruments.

6. The fluid treatment system of claim 3, wherein the UV source is removably coupled to the main fluid supply line.

7. The fluid treatment system of claim 3, wherein the UV source is selected from a group consisting of an LED light, an electron beam device, and a miniature xenon flash lamp.

8. The fluid treatment system of claim 3, wherein the UV source includes
 a conduit adapted to carry the fluid and having a first index of refraction;
 a sheath surrounding the conduit and having a second index of refraction, the second index of refraction being lower than the first index of refraction, and
 a light source configured to produce UV light and arranged to send the UV light into the conduit.

9. The fluid treatment system of claim 1, further comprising:
 a delivery unit including a dental instrument holder;
 wherein the dental instrument is engagable with the dental instrument holder;
 a quick-connect coupling engagable with the dental instrument;
 wherein the fluid supply line is engagable with the quick-connect coupling and in fluid communication with the dental instrument;
 wherein the UV source is a first UV source; and
 a second UV source disposed adjacent the quick-connect coupling, the second UV source positioned to be in fluid communication with the fluid such that UV light from the second UV source disinfects the fluid.

10. The fluid treatment system of claim 9, wherein the fluid supply line includes a main fluid supply line and a plurality of individual fluid supply lines extending from the main fluid supply line, and wherein the first UV source is coupled to one of the individual fluid supply lines.

11. The fluid treatment system of claim 9, wherein the fluid supply line includes a main fluid supply line and a plurality of individual fluid supply lines extending from the main fluid supply line, and wherein the first UV source is coupled to the main fluid supply line.

12. The fluid treatment system of claim 9, wherein the dental instrument is a first dental instrument and the coupling is a first coupling, and further comprising a second dental instrument engagable with the dental instrument holder, wherein the second coupling is engagable with the second dental instrument.

13. The fluid treatment system of claim 12, further comprising a third UV source disposed adjacent the second coupling.

14. The fluid treatment system of claim 3, wherein the dental instrument holder includes an activation element that is configured to turn the UV source on and off.

15. The fluid treatment system of claim 9, wherein the dental instrument holder includes an activation element that is configured to turn the first and second UV sources on and off.

16. The fluid treatment system of claim 1, wherein the UV source includes a cylindrical housing, wherein the sheath is a cylindrical sheath disposed within the housing, wherein the conduit is a cylindrical conduit disposed within the sheath, and wherein at one end of the sheath, a radial gap is disposed between the sheath and the housing, the gap defining a collection chamber for the fluid.

* * * * *